United States Patent
Lee et al.

(10) Patent No.: US 10,610,560 B2
(45) Date of Patent: Apr. 7, 2020

(54) METHOD OF INDEPENDENT OR ADJUVANT TREATMENT OF PARKINSON'S DISEASE AND PARKINSON'S SYNDROME

(71) Applicant: Chen-Yu Lee, Taipei (TW)

(72) Inventors: Chen-Yu Lee, Taipei (TW); Che-Hao Wu, Taipei (TW); Yao-Nan Yuan, New Taipei (TW); Chuang-Hsin Chiu, Taipei (TW); Yan-Chih Liao, Taipei (TW); Yu-Ming Fan, Taipei (TW); Yuan-Hao Chen, Taipei (TW); Dueng-Yuan Hueng, Taipei (TW)

(73) Assignee: Chen-Yu Lee, Taipei (TW)

( * ) Notice: Subject to any disclaimer, the term of this patent is extended or adjusted under 35 U.S.C. 154(b) by 319 days.

(21) Appl. No.: 15/859,983

(22) Filed: Jan. 2, 2018

(65) Prior Publication Data

US 2019/0201472 A1    Jul. 4, 2019

(51) Int. Cl.
| | | |
|---|---|---|
| *A61K 36/8888* | (2006.01) | |
| *A61K 36/076* | (2006.01) | |
| *A61K 36/484* | (2006.01) | |
| *A61K 36/284* | (2006.01) | |
| *A61K 36/884* | (2006.01) | |
| *A61K 36/752* | (2006.01) | |
| *A61P 25/16* | (2006.01) | |
| *A61K 36/9068* | (2006.01) | |
| *A61K 36/756* | (2006.01) | |
| *A61K 36/8988* | (2006.01) | |
| *A61K 36/714* | (2006.01) | |
| *A61K 36/232* | (2006.01) | |
| *A61K 36/481* | (2006.01) | |
| *A61K 36/8998* | (2006.01) | |

(52) U.S. Cl.
CPC ........ *A61K 36/8888* (2013.01); *A61K 36/076* (2013.01); *A61K 36/232* (2013.01); *A61K 36/284* (2013.01); *A61K 36/481* (2013.01); *A61K 36/484* (2013.01); *A61K 36/714* (2013.01); *A61K 36/752* (2013.01); *A61K 36/756* (2013.01); *A61K 36/884* (2013.01); *A61K 36/8988* (2013.01); *A61K 36/8998* (2013.01); *A61K 36/9068* (2013.01); *A61P 25/16* (2018.01)

(58) Field of Classification Search
CPC .............. A61K 2300/00; A61K 36/076; A61K 36/232; A61K 36/284; A61K 36/481; A61K 36/484; A61K 36/714; A61K 36/752; A61K 36/756; A61K 36/884; A61K 36/8888; A61K 36/8988; A61K 36/8998; A61K 36/9068; A61P 25/16
See application file for complete search history.

(56) References Cited

U.S. PATENT DOCUMENTS 8,003,140 B1 *   8/2011   Lee ...................... A61K 36/076
                                                                424/725

* cited by examiner

*Primary Examiner* — Aaron J Kosar
(74) *Attorney, Agent, or Firm* — Bacon & Thomas, PLLC

(57) ABSTRACT

The present invention is directed to a therapeutic method of independent or adjuvant treatment of Parkinson's disease and Parkinson's syndrome, comprising administering to a subject in need a therapeutically effective amount of Chinese medicine composition, wherein the Chinese medicine composition comprises the extract of the mixture of Rhizoma Pinelliae, Rhizoma Atractylodis Macrocephalae, Poria, Radix Glycyrrhizae, Rhizoma Atractylodis, Rhizoma Alismatis, Pericarpium Citri Reticulatae, Massa Medicata Fermentata, Fructus Hordei Germinatus, Rhizoma Zingiberis, Cortex Phellodendri, rhizoma Gastrodiae, Radix Aconiti Lateralis Praeparata, Radix Angelicae Sinensis, and Radix Astragali.

12 Claims, 2 Drawing Sheets

METHOD OF INDEPENDENT OR ADJUVANT TREATMENT OF PARKINSON'S DISEASE AND PARKINSON'S SYNDROME

BACKGROUND OF THE INVENTION

1. Field of the Invention

The present invention is directed to a method of independent or adjuvant treatment of Parkinson's disease and Parkinson's syndrome; in particular, a method of increasing the proliferation and signal transduction of dopaminergic cell in brain.

2. Description of Related Art

The application of Chinese herbal medicine in treatment of diseases attracts significant attentions for a long time. In recent years, the Chinese medicine is also applied to treatment of some neurological diseases. In general, traditional Chinese medicines comprise many components, usually extract of raw natural occurred material with each presents in very small quantity. From the Western medicine point of view, the advantage of this multiple component medicine is to have fewer side effects when any one component is given in large quantity.

Parkinson's disease or Parkinson's syndrome is a common long-term disease attributed to degeneration of central nerve system, mainly impairing the function of motor nerve system. The major cause of Parkinson's disease or Parkinson's syndrome is still unknown while it is mostly related to genetic and environmental factors.

The typical symptoms of Parkinson's disease or Parkinson's syndrome is the death of basal ganglia in brain and impairment of dopamine secretory neurons, rendering the reduction of dopamine production.

The major treatment of Parkinson's disease or Parkinson's syndrome is administration of pharmaceuticals, typically L-DOPA, dopamine agonist, or monoamine oxidase inhibitors, etc. For the severe cases, deep brain stimulation is adopted. However, most of the Parkinson's disease or Parkinson's syndrome drug adverse effects.

For the reason above, it is necessary to develop the pharmaceuticals which enhance the proliferation of dopaminergic cell, alleviate the symptoms of Parkinson's disease or Parkinson's syndrome, and provide the better independent or adjuvant therapy.

SUMMARY OF THE INVENTION

The objective of the present invention is to provide a method of independent or adjuvant treatment of Parkinson's disease and Parkinson's syndrome.

The method of independent or adjuvant treatment of Parkinson's disease and Parkinson's syndrome comprises administering to a subject in need a therapeutically effective amount of Chinese medicine composition;
wherein the Chinese medicine composition comprises the extract of the first mixture of Rhizoma Pinelliae, Rhizoma Atractylodis Macrocephalae, Poria, Radix Glycyrrhizae, Rhizoma Atractylodis, Rhizoma Alismatis, Pericarpium Citri Reticulatae, Massa Medicata Fermentata, Fructus Hordei Germinatus, Rhizoma Zingiberis, Cortex Phellodendri, rhizoma Gastrodiae, Radix Aconiti Lateralis Praeparata, Radix Angelicae Sinensis, and Radix Astragali.

In a preferred embodiment, the Chinese medicine composition is prepared by the following steps:
providing the first mixture;
mixing the first mixture and water to form a second mixture;
heating the second mixture to obtain a crude extract; and
filtering the crude extract and retaining the liquid, to obtain the Chinese medicine composition.

In a preferred embodiment, the first mixture comprises 2-4 parts by weight of Rhizoma Pinelliae, 2-4 parts by weight of Rhizoma Atractylodis Macrocephalae, 2-4 parts by weight of Poria, 2-4 parts by weight of Radix Glycyrrhizae, 2-4 parts by weight of Rhizoma Atractylodis, 2-4 parts by weight of Rhizoma Alismatis, 2-4 parts by weight of Pericarpium Citri Reticulatae, 2-4 parts by weight of Massa Medicata Fermentata, 2-4 parts by weight of Fructus Hordei Germinatus, 2-4 parts by weight of Rhizoma Zingiberis, 2-4 parts by weight of Cortex Phellodendri, 4-6 parts by weight of rhizoma Gastrodiae, 4-6 parts by weight of Radix Aconiti Lateralis Praeparata, 1-3 parts by weight of Radix Angelicae Sinensis, and 8-12 parts by weight of Radix Astragali.

In a preferred embodiment, the part by weight of the first mixture is 3.75 gram per part.

In a preferred embodiment, the Chinese medicine composition is administered via oral administration, enteral administration, or intravenous injection.

In a preferred embodiment, the Chinese medicine composition further comprises pharmaceutically acceptable carrier, stabilizer, diluent, dispersant, suspending agents, thickening agent, or excipient, or the combination thereof.

Another objective of the present invention is to provide a method of increasing the proliferation and signal transduction of dopaminergic cell in brain, comprising administering to a subject in need a therapeutically effective amount of Chinese medicine composition;

DETAILED DESCRIPTION OF THE PREFERRED EMBODIMENT

Figure 1A:
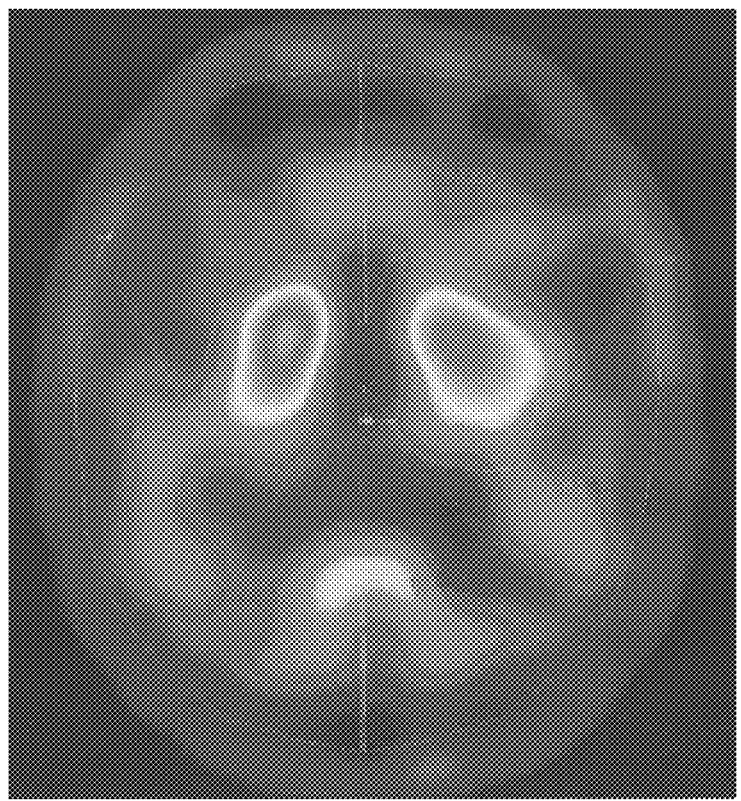
FIGS. 1A-1B show the imaging of frontal lobe, temporal lobe, and occipital lobe by $^{99m}$Tc TRODAT-1 labeling and SPECT before (FIG. 1A) and after (FIG. 1B) the treatment of the Chinese medicine composition of the present invention.

The features of the present invention are set forth with particularity in the appended claims. A better understanding of the features and advantage thereof will be demonstrated by reference to the following detailed description that sets forth illustrative embodiments, in which the principles of the invention are employed.

Certain Pharmaceutical and Medical Terminology

Unless otherwise specified, the following terms used in the specification and claims have the definitions given below. It must be noted that, as used in the specification and the appended claims, the singular forms "a", "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology can be employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described. Unless otherwise indicated, all materials employed in the present invention are available in the ordinary markets.

The method according to the present invention can be independently or adjuvantly used to treat Parkinson's disease or Parkinson's syndrome; in particular used to treat the symptoms thereof including but not limited to body shaking, spasticity, slowness of movement, speech problem, depression, cognitive deficit, and memory loss.

The term "carrier" or "excipient" or the like, as used herein, refers to relatively nontoxic chemical compounds or agents that facilitate the incorporation of a compound into cells or tissues without interfering the effect of the treatment.

The term "diluent" or the like, as used herein, refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The aforementioned pharmaceutical vehicles can further comprise at least one selected from the group consisting of aromatics, buffering agents, binders, colorants, disintegrants, emulsifiers, extenders, flavor-improving agents, gellants, glidants, preservatives, skin-penetration enhancers, solubilizers, stabilizers, dispersing agents, suspending agents, sweeteners, tonicity agents, viscosity-increasing agents, or the combination thereof.

The term "pharmaceutically acceptable", as used herein, refers to the compounds, formulations, composition, and/or dose form, within the scope of reasonable medical judgment, suitable for contacting with the suffered subject, without undue detrimental effect, toxicity, irritation, allergic response, or any conditions or complications on the general health of the subject being treated, and commensurate with a reasonable benefit/risk ratio.

The term "effective amount" or "therapeutically effective amount", as used herein, refers to a sufficient amount of an agent or a compound being administered which will relieve one or more of the symptoms of the disease or condition being treated to some extent; the result thereof can be reduction and/or alleviation of the signs, symptoms, or causes of a disease, or any other desired alteration of a biological system. For example, an "effective amount" for therapeutic uses is the amount of the composition as disclosed herein required to provide a clinically significant decrease in disease symptoms. An appropriate "effective" amount in any individual case may be determined using techniques, such as a dose escalation study.

The term "enhance", "enhancing", or the like, as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

The term "treat," "treating", "treatment", or the like, as used herein, include alleviating, abating or ameliorating at least one symptom of a disease or condition, preventing disease progression, inhibiting the disease or condition, e.g., arresting the development of the disease or condition, relieving the disease or condition, causing regression of the disease or condition, relieving the condition caused by the disease or condition, or reducing the sign or symptoms of the disease or condition either prophylactically and/or therapeutically.

The any mentioned or suggested ranges are merely suggestive, as the number of variables in regard to an individual treatment regime is large, and considerable excursions from these recommended values are not uncommon. The dosages may be altered depending on a number of variables, not limited to the activity of the compound used, the disease or condition to be treated, the mode of administration, the requirements of the individual subject, the severity of the disease, and the judgment of the physicians.

The present invention provides an method of independent or adjuvant treatment of Parkinson's disease and Parkinson's syndrome, comprising administering to a subject in need a therapeutically effective amount of Chinese medicine composition, wherein the Chinese medicine composition comprises the extract of the first mixture of Rhizoma Pinelliae, Rhizoma Atractylodis Macrocephalae, Poria, Radix Glycyrrhizae, Rhizoma Atractylodis, Rhizoma Alismatis, Pericarpium Citri Reticulatae, Massa Medicata Fermentata, Fructus Hordei Germinatus, Rhizoma Zingiberis, Cortex Phellodendri, rhizoma Gastrodiae, Radix Aconiti Lateralis Praeparata, Radix Angelicae Sinensis, and Radix Astragali.

The present invention further provides a method of increasing the proliferation and signal transduction of dopaminergic cell in brain, comprising administering to a subject in need a therapeutically effective amount of the aforementioned Chinese medicine composition according to the present invention.

The present invention further provides a method of inducing the expression of dopamine transporter (DAT), comprising administering to a subject in need a therapeutically effective amount of the aforementioned Chinese medicine composition according to the present invention.

In an embodiment, the Chinese medicine composition can be co-administered with another pharmaceutical composition according to the method of treatment of uremia. In a particular embodiment, the Chinese medicine composition and another pharmaceutical composition are administered simultaneously, concurrently or sequentially.

In a particular embodiment, the said pharmaceutical composition comprises the pharmaceuticals used to treat Parkinson's disease and Parkinson's syndrome which is reported in prior art, including but not limited to L-DOPA, methyldopa, ethyldopa, dopamine agonist (such as pramipexole, ropinirole, apomorphine, rotigotine, lisuride, bromocriptine, cabergoline, or pergolide), and Monoamine oxidase (MAO) inhibitors (such as selegiline or rasagiline).

The term "independent or adjuvant" used herein means that the method of treatment according to the present invention can be used to treat Parkinson's disease and Parkinson's syndrome alone without another therapy; or, can be combined with other therapy of Parkinson's disease and Parkinson's syndrome.

The materials and preparation of Chinese medicine composition

The Chinese medicine composition used herein comprises the extract of the first mixture comprising the following materials: 2-4 parts by weight of Rhizoma Pinelliae(Pinellia ternata), 2-4 parts by weight of Rhizoma Atractylodis Macrocephalae, 2-4 parts by weight of Poria (*Wolfiporia cocos*), 2-4 parts by weight of Radix Glycyrrhizae (*Glycyrrhiza uralensis Fisch.* or *G. inflata* or *G. glabra*), 2-4 parts by weight of Rhizoma Atractylodis (*Atractylodes lancea* or *A.* chinensis), 2-4 parts by weight of Rhizoma Alismatis (*Alisma orientalis*), 2-4 parts by weight of Pericarpium Citri Reticulatae (*Citrus reticulata*), 2-4 parts by weight of Massa Medicata Fermentata, 2-4 parts by weight of Fructus Hordei Germinatus (*Hordeum vulgare*), 2-4 parts by weight of Rhizoma Zingiberis (*Zingiber officinale*), 2-4 parts by weight of Cortex Phellodendri (*Phellodendron amurense* or *P. chinense*), 4-6 parts by weight of rhizoma Gastrodiae (*Gastrodia elata*), 4-6 parts by weight of Radix Aconiti Lateralis Praeparata (*Acontium carmichaeli*), 1-3 parts by weight of Radix Angelicae Sinensis (*Angelica sinensis*), and 8-12 parts by weight of Radix Astragali (*Astragalus membranaceus* or *A. membranaceus*); wherein it is a daily dose of the Chinese medicine composition when a part by weight of the first mixture is 3.75g per part.

In specific, the Chinese medicine composition used herein comprises the extract of the first mixture comprising the following materials: 3 parts by weight of Rhizoma Pinelliae, 3 parts by weight of Rhizoma Atractylodis Macrocephalae, 3 parts by weight of Poria, 3 parts by weight of Radix Glycyrrhizae, 3 parts by weight of Rhizoma Atractylodis, 3 parts by weight of Rhizoma Alismatis, 3 parts by weight of Pericarpium Citri Reticulatae, 3 parts by weight of Massa Medicata Fermentata, 3 parts by weight of Fructus Hordei Germinatus, 3 parts by weight of Rhizoma Zingiberis, 3 parts by weight of Cortex Phellodendri, 5 parts by weight of rhizoma Gastrodiae, 5 parts by weight of Radix Aconiti Lateralis Praeparata, 2 parts by weight of Radix Angelicae Sinensis, and 10 parts by weight of Radix Astragali; wherein it is a daily dose of the Chinese medicine composition when a part by weight of the first mixture is 3.75 g per part.

The components of the first mixture are heated and extracted in a solvent; wherein the component of the first mixture can be optionally grinded before extraction to achieve the best extraction outcome. The preferred solvent of the extraction is water, ethanol, DMSO (Dimethyl sulfoxide), or the combination thereof.

In a preferred embodiment of the present invention, the components of the daily dose of the Chinese herbal medicine are dissolved in 1,800-2,200 ml water to obtain a second mixture; the second mixture is heated at 100-120° C. for 1 hour and then the residue is filtered out to obtain the liquid extract. Preferably, the liquid extract is equally divided into 3 doses for ter in die administration. Preferably, the second mixture is heated at 100-120° C. for 1 hour and then the volume of the liquid extract after filtration is 400-500 ml.

Furthermore, the preparation method of the Chinese herbal medicine can include the step of concentration as follows: after the residue of the extract is filtered out, the liquid extract is condensed by vacuum or low pressure concentration under the condition of 50-60° C. and 20-40 torr, in order to obtain the condensate; preferably, the volume of the condensate is 1/10-1/20 volume of the liquid extract.

Furthermore, the corn starch used as an excipient is added to the condensate to obtain Chinese herbal paste; wherein the quantity of the corn starch depends on the stability of condensate; wherein the paste is optionally subject to granulation by spray-drying method.

EXAMPLE 1

The materials and methods in the example include $^{99m}$Tc TRODAT-1 labeling and single photon emission computed tomography (SPECT), which are used to image dopamine transporter (DAT), and generally used to scan the DAT in central nerve system and diagnose neurodegenerative disease such as Parkinson's disease and Parkinson's syndrome. The details can be referred to in the prior report (Kung et al. Eur J Nucl Med 1997 and Weng et al. J Nucl Med 2004).

The patient suffered from Parkinson's disease and Parkinson's syndrome (who does not take any drugs of Parkinson's disease and Parkinson's syndrome) is administered the Chinese medicine composition according to the present invention for one dose per day. After 5 months administration, $^{99m}$Tc TRODAT-1 labeling and SPECT is employed to image the DAT in central nerve system, comparing the imaging ratio of frontal lobe, temporal lobe, and occipital lobe in the patient's brain image. The result shows in FIG. 1A (before treatment) and FIG. 1B (post treatment), while table 1 shows the quantitative result thereof.

TABLE 1

|  |  | ratio before treatment | ratio post treatment | post/before ratio |
| --- | --- | --- | --- | --- |
| Frontal lobe | R | 0.1 | 0.21 | 2.1 |
|  | L | 0.13 | 0.23 | 1.769 |
| Temporal lobe | R | 0.25 | 0.36 | 1.44 |
|  | L | 0.24 | 0.32 | 1.333 |
| Occipital lobe | R | 0.24 | 0.3 | 1.25 |
|  | L | 0.16 | 0.32 | 2 |

$P = 0.0003 (p < 0.05)$
R: right brain;
L: left brain

Figure 1B:

According to FIG. 1A-1B and table 1, after the patient of Parkinson's disease and Parkinson's syndrome is administered the Chinese medicine composition according to the present invention for 5 months, the scanning of the patient's brain image shows that the DAT in the frontal lobe, temporal lobe, and occipital lobe significantly increase (p<0.05). This result indicates that administration of the Chinese medicine composition according to the present invention can effectively alleviate Parkinson's disease and Parkinson's syndrome.

EXAMPLE 2

In addition to the imaging in example 1, $^{99m}$Tc TRODAT-1 labeling and SPECT is employed to image the DAT in central nerve system, comparing the imaging ratio of caudate nucleus and putamen. The result shows in FIG. 2A (before treatment) and FIG. 2B (post treatment), while table 2 shows the quantitative result thereof.

TABLE 2

|  |  | ratio before treatment | ratio post treatment |
| --- | --- | --- | --- |
| Caudate nucleus | R | 0.77 | 0.90 |
|  | L | 0.71 | 0.68 |
| putamen | R | 0.59 | 0.33 |
|  | L | 0.62 | 0.65 |
| Mean | R | 0.68 | 0.62 |
|  | L | 0.67 | 0.67 |

$P < 0.05$

Figure 2A:
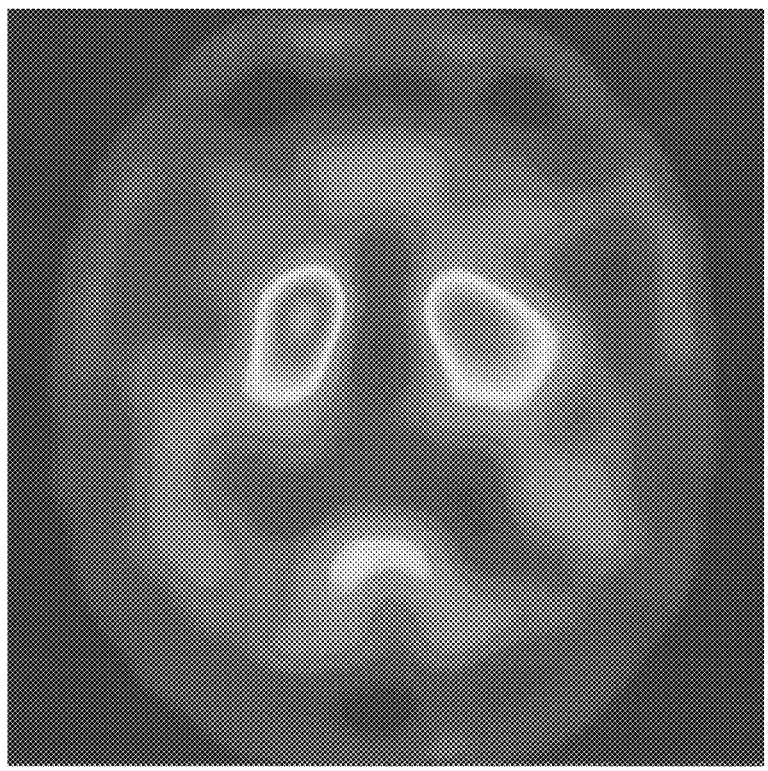
FIGS. 2A-2B show the imaging of caudate nucleus and putamen by $^{99m}$Tc TRODAT-labeling and SPECT before (FIG. 2A) and after (FIG. 2B) the treatment of the Chinese medicine composition of the present invention.
Figure 2B:
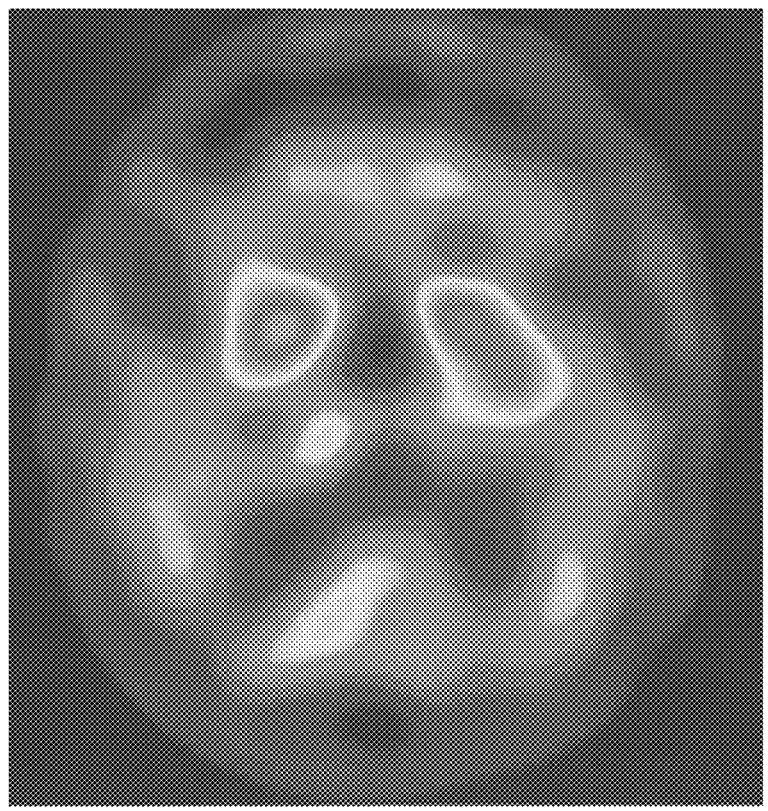

According to FIG. 2A-2B, after the patient of Parkinson's disease and Parkinson's syndrome is administered the Chinese medicine composition according to the present invention, the scanning of the patient's brain image shows that the DAT in caudate nucleus and putamen significantly increases (p<0.05). This result indicates that administration of the Chinese medicine composition according to the present invention can effectively alleviate Parkinson's disease and Parkinson's syndrome.

In conclusion, according to the result of $^{99}$mTc TRO-DAT-1 labeling and SPECT method, the Chinese medicine composition according to the present invention can effectively increase the expression of DAT in central nerve system, and can be further used to treat and alleviate Parkinson's disease and Parkinson's syndrome.

While the preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents are covered thereby.

What is claimed is:

1. A method of independent or adjuvant treatment of Parkinson's disease and Parkinson's syndrome, comprising administering to a subject in need a therapeutically effective amount of Chinese medicine composition;
   wherein the Chinese medicine composition comprises the extract of the first mixture of Rhizoma Pinelliae, Rhizoma Atractylodis Macrocephalae, Poria, Radix Glycynhizae, Rhizoma Atractylodis, Rhizoma Alismatis, Pericarpium Citri Reticulatae, Massa Medicata Fermentata, Fructus Hordei Germinatus, Rhizoma Zingiberis, Cortex Phellodendri, rhizoma Gastrodiae, Radix Aconiti Lateralis Praeparata, Radix Angelicae Sinensis, and Radix Astragali.

2. The method as claimed in claim 1, wherein the Chinese medicine composition is prepared by the following steps:
   providing the first mixture;
   mixing the first mixture and water to form a second mixture;
   heating the second mixture to obtain a crude extract; and
   filtering the crude extract and retaining the liquid, to obtain the Chinese medicine composition.

3. The method as claimed in claim 1, wherein the first mixture comprises 2-4 parts by weight of Rhizoma Pinelliae, 2-4 parts by weight of Rhizoma Atractylodis Macrocephalae, 2-4 parts by weight of Poria, 2-4 parts by weight of Radix Glycyrrhizae, 2-4 parts by weight of Rhizoma Atractylodis, 2-4 parts by weight of Rhizoma Alismatis, 2-4 parts by weight of Pericarpium Citri Reticulatae, 2-4 parts by weight of Massa Medicata Fennentata, 2-4 parts by weight of Fructus Hordei Germinatus, 2-4 parts by weight of Rhizoma Zingiberis, 2-4 parts by weight of Cortex Phellodendri, 4-6 parts by weight of rhizoma Gastrodiae, 4-6 parts by weight of Radix Aconiti Lateralis Praeparata, 1-3 parts by weight of Radix Angelicae Sinensis, and 8-12 parts by weight of Radix Astragali.

4. The method as claimed in claim 3, wherein the part by weight of the first mixture is 3.75 gram per part.

5. The method as claimed in claim 1, wherein the Chinese medicine composition is administered via oral administration, enteral administration, or intravenous injection.

6. The method as claimed in claim 1, wherein the Chinese medicine composition further comprises pharmaceutically acceptable carrier, stabilizer, diluent, dispersant, suspending agents, thickening agent, or excipient, or the combination thereof.

7. A method of increasing the proliferation and signal transduction of dopaminergic cell in brain, comprising administering to a subject in need a therapeutically effective amount of Chinese medicine composition;
   wherein the Chinese medicine composition comprises the extract of the first mixture of Rhizoma Pinelliae, Rhizoma Atractylodis Macrocephalae, Poria, Radix Glycynthizae, Rhizoma Atractylodis, Rhizoma Alismatis, Pericarpium Citri Reticulatae, Massa Medicata Fermentata, Fructus Hordei Germinatus, Rhizoma Zingiberis, Cortex. Phellodendri, rhizoma Gastrodiae, Radix Aconiti Lateralis Praeparata, Radix Angelicae Sinensis, and Radix Astragali.

8. The method as claimed in claim 7, wherein the Chinese medicine composition is prepared by the following steps:
   providing the first mixture;
   mixing the first mixture and water to form a second mixture;
   heating the second mixture to obtain a crude extract; and
   filtering the crude extract and retaining the liquid, to obtain the Chinese medicine composition.

9. The method as claimed in claim 7, wherein the first mixture comprises 2-4 parts by weight of Rhizoma Pinelliae, 2-4 parts by weight of Rhizoma Atractylodis Macrocephalae, 2-4 parts by weight of Poria, 2-4 parts by weight of Radix Glycyrrhizae, 2-4 parts by weight of Rhizoma Atractylodis, 2-4 parts by weight of Rhizoma Alismatis, 2-4 parts by weight of Pericarpium Citri Reticulatae, 2-4 parts by weight of Massa Medicata Fennentata, 2-4 parts by weight of Fructus Hordei Germinatus, 2-4 parts by weight of Rhizoma Zingiberis, 2-4 parts by weight of Cortex Phellodendri, 4-6 parts by weight of rhizoma Gastrodiae, 4-6 parts by weight of Radix Aconiti Lateralis Praeparata, 1-3 parts by weight of Radix Angelicae Sinensis, and 8-12 parts by weight of Radix Astragali.

10. The method as claimed in claim 9, wherein the part by weight of the first mixture is 3.75 gram per part.

11. The method as claimed in claim 7, wherein the Chinese medicine composition is administered via oral administration, enteral administration, or intravenous injection.

12. The method as claimed in claim 7, wherein the Chinese medicine composition further comprises pharmaceutically acceptable carrier, stabilizer, diluent, dispersant, suspending agents, thickening agent, or excipient, or the combination thereof.

* * * * *